(12) United States Patent
Xiao et al.

(10) Patent No.: US 7,495,123 B2
(45) Date of Patent: *Feb. 24, 2009

(54) PROCESS FOR THE PREPARATION OF ENANTIOMERICALLY ENRICHED BETA AMINO ACID DERIVATIVES

(75) Inventors: Yi Xiao, Fanwood, NJ (US); Yongkui Sun, Bridgewater, NJ (US); Thorsten Rosner, Berkeley Heights, NJ (US); Nelo R. Rivera, New Milford, NJ (US); Shane W. Krska, New Providence, NJ (US); Andrew M. Clausen, Westfield, NJ (US); Joseph D. Armstrong, III, Westfield, NJ (US); Felix Spindler, Starrkirch-Wil (CH); Christophe Malan, Neuchatel (CH)

(73) Assignees: Solvias AG, Basel (CH); Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/547,183

(22) PCT Filed: Apr. 5, 2005

(86) PCT No.: PCT/US2005/011585

§ 371 (c)(1),
(2), (4) Date: Jun. 4, 2007

(87) PCT Pub. No.: WO2005/097733

PCT Pub. Date: Oct. 20, 2005

(65) Prior Publication Data

US 2008/0058522 A1    Mar. 6, 2008

Related U.S. Application Data

(60) Provisional application No. 60/646,698, filed on Jan. 24, 2005, provisional application No. 60/559,514, filed on Apr. 5, 2004.

(51) Int. Cl.
*C07C 229/00* (2006.01)
*C07C 205/00* (2006.01)

(52) U.S. Cl. .................. 560/155; 562/553
(58) Field of Classification Search .......... None
See application file for complete search history.

(56) References Cited

U.S. PATENT DOCUMENTS

| | | | |
|---|---|---|---|
| 5,563,309 A | 10/1996 | Togni et al. | |
| 6,258,979 B1 | 7/2001 | Kagan et al. | |
| 6,284,925 B1 | 9/2001 | Knochel et al. | |
| 6,492,544 B2 | 12/2002 | Krimmer et al. | |
| 6,699,871 B2 | 3/2004 | Edmondson et al. | |
| 7,015,348 B2 | 3/2006 | Matsumura et al. | |
| 2004/0023344 A1* | 2/2004 | Matsumura et al. | 435/106 |
| 2004/0167339 A1* | 8/2004 | Zhang | 548/101 |
| 2006/0194977 A1 | 8/2006 | Xiao et al. | |

FOREIGN PATENT DOCUMENTS

| | | |
|---|---|---|
| EP | 1 103 536 A1 | 5/2001 |
| EP | 1 389 901 A1 | 2/2004 |
| WO | WO 02/40491 A1 | 5/2002 |
| WO | WO 03/004498 A1 | 1/2003 |
| WO | WO 2004/085378 A1 | 10/2004 |

OTHER PUBLICATIONS

Zhu, G. et al, "Highly Efficient Asymmetric Synthesis of B-Amino Acid Derivatives via Rhodium-Catalyzed Hydrogenation of B-(Acylamino)acrylates", J. Org. Chem, vol. 64, pp. 6907-6910, 1999.
Lubell, W. et al, "Enantioselective Synthesis of B-Amino Acids Based on BINAP-Ruthenium(II) Catalyzed Hydrogenation" Tetrahedron: Asymmetry, vol. 2, No. 7, pp. 543-554, 1991.
Hsiao, Y. et al, "Highly Efficient Synthesis of B-Amino Acid Derivatives via Asymmetric Hydrogenation of Unprotected Enamines", J. Am. Chem. Soc., vol. 126, pp. 9918-9919, 2004.
Hayashi, T. et al. "Asymmetric Synthesis Catalyzed by Chiral Ferrocenylphosphine-Transition Metal Complexes. I. Preparation of Chiral Ferrocenylphosphines" Bull. Chem. Soc. Jpn, vol. 53, pp. 1138-1151, 1980.

\* cited by examiner

*Primary Examiner*—Karl J Puttlitz
(74) *Attorney, Agent, or Firm*—Philippe L. Durette; Catherine D. Fitch

(57) ABSTRACT

The present invention relates to a process for the efficient preparation of enantiomerically enriched beta amino acid derivatives wherein the amino group is unprotected. The product chiral beta amino acid derivatives are useful in the asymmetric synthesis of biologically active molecules. The process comprises an enantioselective hydrogenation of an amine-unprotected prochiral beta-amino acrylic acid or derivative thereof in the presence of a rhodium metal precursor complexed with a chiral mono- or bisphosphine ligand.

15 Claims, No Drawings

PROCESS FOR THE PREPARATION OF ENANTIOMERICALLY ENRICHED BETA AMINO ACID DERIVATIVES

CROSS REFERENCE TO RELATED APPLICATIONS

This application is the National Stage of International Application No. PCT/US05/11585, filed Apr. 5, 2005, which claims the benefit under 35 U.S.C. 119(e) of U.S. Provisional Application No. 60/559,514, filed Apr. 5, 2004, and Provisional Application No. 60/646,698, filed Jan. 24, 2005.

FIELD OF THE INVENTION

The present invention relates to a process for the efficient preparation of enantiomerically enriched beta amino acid derivatives wherein the amino group is unprotected. The product chiral beta amino acid derivatives are frequent constituents of drug candidates and are also useful in the asymmetric synthesis of other biologically active molecules. The process comprises an enantioselective hydrogenation of an amine-unprotected prochiral beta amino acrylic acid or derivative thereof in the presence of a rhodium metal precursor complexed with a chiral mono- or bisphosphine ligand.

BACKGROUND OF THE INVENTION

The present invention provides an efficient process for the preparation of beta amino acid derivatives of structural formula I:

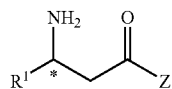

(I)

enantiomerically enriched at the carbon atom marked with an *; wherein $Z$ is $OR^2$, $SR^2$, or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, N, NH, and $NC_{1-4}$ alkyl, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one to five fluorines; and said heterocyclic ring system being optionally fused with a 5- to 6-membered saturated or aromatic carbocyclic ring system or a 5- to 6-membered saturated or aromatic heterocyclic ring system containing one to three heteroatoms selected from O, S, N, NH, and $NC_{1-4}$ alkyl, said fused ring system being unsubstituted or substituted with one to four substituents selected from hydroxy, amino, fluorine, $C_{1-4}$ alkyl, and $C_{1-4}$ alkoxy, wherein alkyl and alkoxy are unsubstituted or substituted with one to five fluorines.

The process of the present invention relates to a method for the preparation of chiral beta amino acid derivatives of structural formula I in an efficient enantioselective fashion via rhodium metal-catalyzed asymmetric hydrogenation of a prochiral enamine of structural formula II:

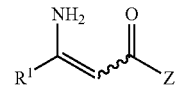

(II)

in the presence of a chiral mono- or bisphosphine ligand, with the provisos that
(1) the chiral bisphosphine ligand is not a ferrocenyl bisphosphine ligand of structural formula III:

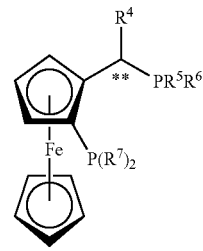

(III)

wherein $R^4$ is $C_{1-4}$ alkyl or aryl;
$R^5$ and $R^6$ are each independently $C_{1-6}$ alkyl, $C_{5-12}$ cycloalkyl, or aryl; and
$R^7$ is $C_{1-4}$ alkyl or unsubstituted phenyl; and
(2) the chiral bisphosphine ligand is not a ligand selected from the group consisting of:
1,2-bis(anisylphenylphosphino)ethane (DIPAMP);
1,2-bis(alkylmethylphosphino)ethane (BisP*);
2,3-bis(diphenylphosphino)butane (CHIRAPHOS);
1,2-bis(diphenylphosphino)propane (PROPHOS);
2,3-bis(diphenylphosphino)-5-norbornene (NORPHOS);
2,3-O-isopropylidene-2,3-dihydroxy-1,4-bis-(diphenylphosphino)butane (DIOP);
1-cyclohexyl-1,2-bis(diphenylphosphino)ethane (CYCPHOS);
1-substituted-3,4-bis(diphenylphosphino)pyrrolidine (DEGPHOS);
2,4-bis(diphenylphosphino)pentane (SKEWPHOS);
1,2-bis(substituted phospholano)benzene (DuPHOS);
1,2-bis(substituted phospholano)ethane (BPE);
1-(substituted phospholano)-2-(diphenylphosphino)benzene (UCAP-Ph);
1-(bis(3,5-dimethylphenyl)phosphino)-2-(substituted phospholano)benzene (UCAP-DM);
1-(substituted phospholano)-2-(bis(3,5-di(t-butyl)-4-methoxyphenyl)phosphino)benzene (UCAP-DTBM);
1-(substituted phospholano)-2-(di-naphthalen-1-yl-phosphino)benzene (UCAP-(1-Nap));
2,2'-bis(diphenylphosphino)-1,1'-binaphthyl (BINAP);
2,2'-bis(di-p-tolylphosphino)-1,1'-binaphthyl (TOL-BINAP);
2,2'-bis(di(3,5-dimethylphenyl)phosphino)-1,1'-binaphthyl (DM-BINAP);
2,2'-bis(diphenylphosphino)-6,6'-dimethyl-1,1'-biphenyl (BICHEP);
((5,6),(5',6')-bis(methylenedioxy)biphenyl-2,2'-diyl)(bisdiphenylphosphine) (SEGPHOS);
((5,6),(5',6')-bis(methylenedioxy)biphenyl-2,2'-diyl)(bis(3,5-dimethylphenyl)phosphine) (DM-SEGPHOS);

((5,6),(5',6')-bis(methylenedioxy)biphenyl-2,2'-diyl)(bis(3,5-di(t-butyl)phenyl)phosphine) (DTBM-SEGPHOS);
cyclohexylanisylmethylphosphine (CAMP);
1-[1',2-bis(diphenylphosphino)ferrocenyl]ethylamine (BP-PFA);
1-[1',2-bis(diphenylphosphino)ferrocenyl]ethyl alcohol (BP-PFOH);
2,2'-bis(diphenylphosphino)-1,1'-dicyclopentane (BICP); and
2,2'-bis(diphenylphosphino)-1,1'-(5,5',6,6',7,7',8,8'-octahydrobinaphthyl ($H_8$-BINAP).

Methods for asymmetrically reducing enamine carbon-carbon double bonds (C=C—N) using chiral ferrocenyl bisphosphines as ligands complexed to a rhodium or iridium metal species have been described in the patent literature (See U.S. Pat. No. 5,563,309 issued Oct. 8, 1996 to Ciba-Geigy Corp. and the related family of patents and patent applications). A related approach to N-acylated beta amino acids using a rhodium DuPHOS catalytic complex has also been disclosed (See U.S. Pat. No. 6,492,544, assigned to Degussa AG). The following publications also describe the asymmetric hydrogenation of N-acylated beta-amino acrylic acids with rhodium metal species complexed to a chiral phosphine ligand: (1) T. Hayashi, et al., *Bull. Chem. Soc. Japan*, 53: 1136-1151 (1980); (2) G. Zhu et al., *J. Org. Chem.*, 64: 6907-6910 (1999); (3) W. D. Lubell, et al., *Tetrahedron: Asymmetry*, 2: 543-554 (1991); and (4) U.S. Pat. No. 6,492,544 (assigned to Degussa AG). In these references all the examples provided have the enamine amino group in the beta-amino acrylic acid substrate for the reaction protected as an acylated derivative. The requirement for amine protection introduces two additional chemical steps into the sequence, namely protection and deprotection, and the synthesis of the protected substrate may also be difficult. The process of the present invention circumvents the need for protecting the amino group in the substrate for the asymmetric hydrogenation reaction and proceeds with excellent reactivity and enantioselectivity.

A process for the preparation of optically active piperazine-2-carboxylic acid derivatives using a metallocenylphosphine ligand has been disclosed in U.S. Pat. No. 5,886,181 (assigned to Lonza, Ltd.).

The product chiral beta-amino acid derivatives are frequent constituents of drug candidates and biologically active peptides which exhibit antibiotic, antifungal, cytotoxic, and other pharmacological properties. They are therefore commonly employed as chiral building blocks in organic synthesis [see G. Cardillo and C. Tomasini, *Chem. Soc. Rev.*, 117-128 (1996)]. Another important application is the substitution of unnatural alpha- and beta-amino acids in biologically active peptides, which greatly enhance the understanding of enzyme mechanisms, protein conformations and properties related to molecular recognition, and for obtaining peptides with increased potency and enzymatic stability.

SUMMARY OF THE INVENTION

The present invention is concerned with a process for the preparation of enantiomerically enriched amine-unprotected beta amino acid derivatives of structural formula I. The process utilizes an asymmetric hydrogenation of a prochiral beta amino acrylic acid or derivative thereof, wherein the enamine amino group is unprotected, in the presence of a rhodium metal precursor complexed with a chiral mono- or bisphosphine ligand. The process of the present invention is applicable to the preparation of beta-amino acid derivatives on a pilot plant or industrial scale. The derived beta amino acids are useful as drug candidates or to prepare a wide variety of other biologically active molecules.

DETAILED DESCRIPTION OF THE INVENTION

The present invention provides an efficient process for the preparation of beta amino acid derivatives of structural formula I:

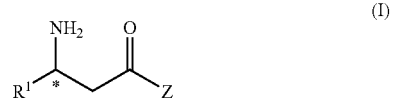

enantiomerically enriched at the carbon atom marked with an *; wherein

Z is $OR^2$, $SR^2$, or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, N, NH, and $NC_{1-4}$ alkyl, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one to five fluorines; and said heterocyclic ring system being optionally fused with a 5- to 6-membered saturated or aromatic carbocyclic ring system or a 5- to 6-membered saturated or aromatic heterocyclic ring system containing one to three heteroatoms selected from O, S, N, NH, and $NC_{1-4}$ alkyl, said fused ring system being unsubstituted or substituted with one to four substituents selected from hydroxy, amino, fluorine, $C_{1-4}$ alkyl, and $C_{1-4}$ alkoxy, wherein alkyl and alkoxy are unsubstituted or substituted with one to five fluorines.

The process of the present invention comprises the step of hydrogenating in the presence of hydrogen gas a prochiral enamine of structural formula II:

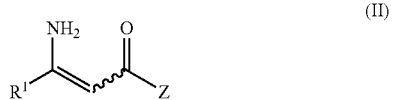

in a suitable organic solvent in the presence of a rhodium metal precursor complexed to a chiral mono- or bisphosphine ligand, with the provisos that (1) the chiral bisphosphine ligand is not a ferrocenyl bisphosphine ligand of structural formula III:

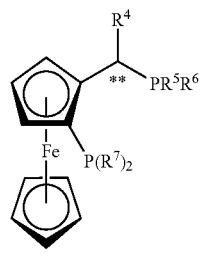

(III)

wherein $R^4$ is $C_{1-4}$ alkyl or aryl;
$R^5$ and $R^6$ are each independently $C_{1-6}$ alkyl, $C_{5-12}$ cycloalkyl, or aryl; and
$R^7$ is $C_{1-4}$ alkyl or unsubstituted phenyl; and that
(2) the chiral bisphosphine ligand is not a ligand selected from the group consisting of:
1,2-bis(anisylphenylphosphino)ethane (DIPAMP);
1,2-bis(alkylmethylphosphino)ethane (BisP*);
2,3-bis(diphenylphosphino)butane (CHIRAPHOS);
1,2-bis(diphenylphosphino)propane (PROPHOS);
2,3-bis(diphenylphosphino)-5-norbornene (NORPHOS);
2,3-O-isopropylidene-2,3-dihydroxy-1,4-bis-(diphenylphosphino)butane (DIOP);
1-cyclohexyl-1,2-bis(diphenylphosphino)ethane (CYCPHOS);
1-substituted-3,4-bis(diphenylphosphino)pyrrolidine (DEGPHOS);
2,4-bis(diphenylphosphino)pentane (SKEWPHOS);
1,2-bis(substituted phospholano)benzene (DuPHOS);
1,2-bis(substituted phospholano)ethane (BPE);
1-(substituted phospholano)-2-(diphenylphosphino)benzene (UCAP-Ph);
1-(bis(3,5-dimethylphenyl)phosphino)-2-(substituted phospholano)benzene (UCAP-DM);
1-(substituted phospholano)-2-(bis(3,5-di(t-butyl)-4-methoxyphenyl)phosphino)benzene (UCAP-DTBM);
1-(substituted phospholano)-2-(di-naphthalen-1-yl-phosphino)benzene (UCAP-(1-Nap));
2,2'-bis(diphenylphosphino)-1,1'-binaphthyl (BINAP);
2,2'-bis(di-p-tolylphosphino)-1,1'-binaphthyl (TOL-BINAP);
2,2'-bis(di(3,5-dimethylphenyl)phosphino)-1,1'-binaphthyl (DM-BINAP);
2,2'-bis(diphenylphosphino)-6,6'-dimethyl-1,1'-biphenyl (BICHEP);
((5,6),(5',6')-bis(methylenedioxy)biphenyl-2,2'-diyl)(bisdiphenylphosphine) (SEGPHOS);
((5,6),(5',6')-bis(methylenedioxy)biphenyl-2,2'-diyl)(bis(3,5-dimethylphenyl)phosphine) (DM-SEGPHOS);
((5,6),(5',6')-bis(methylenedioxy)biphenyl-2,2'-diyl)(bis(3,5-di(t-butyl)phenyl)phosphine) (DTBM-SEGPHOS);
cyclohexylanisylmethylphosphine (CAMP);
1-[1',2-bis(diphenylphosphino)ferrocenyl]ethylamine (BPPFA);
1-[1',2-bis(diphenylphosphino)ferrocenyl]ethyl alcohol (BPPFOH);
2,2'-bis(diphenylphosphino)-1,1'-dicyclopentane (BICP); and
2,2'-bis(diphenylphosphino)-1,1'-(5,5',6,6',7,7',8,8'-octahydrobinaphthyl ($H_8$-BINAP).

The process of the present invention contemplates that the catalytic complex of the rhodium metal precursor and the chiral phosphine ligand may be either (a) generated in situ by the sequential or contemporaneous addition of the rhodium metal precursor and chiral phosphine ligand to the reaction mixture or (b) pre-formed with or without isolation and then added to the reaction mixture. A pre-formed catalytic complex is represented by the formula:

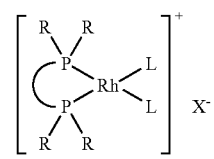

where X represents a non-coordinating anion, such as trifluoromethanesulfonate, tetrafluoroborate, and hexafluorophosphate, and L is a neutral ligand such as an olefin (or chelating di-olefin such as 1,5-cyclooctadiene or norbornadiene) or a solvent molecule (such as MeOH and TFE). In the case where olefin is arene, the complex is represented by the formula:

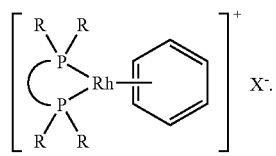

The pre-formed catalytic complex in the case where X represents halogen is represented by the formula:

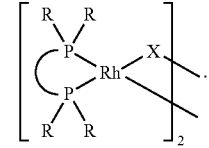

In one embodiment of the process of the present invention, the chiral phosphine ligand has the following structural formula:

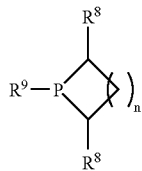

wherein n is 1, 2, or 3; $R^8$ is $C_{1-8}$ alkyl or $C_{6-10}$ aryl; and $R^9$ is aryl or a ferrocenyl phospholane radical.

In one class of this embodiment, $R^9$ is phenyl and $R^8$ is $C_{1-4}$ alkyl or aryl.

A second class of this first embodiment encompasses the FerroLANE, FerroTANE, PhenylLANE, and PhenylTANE series having the following structural formulae:

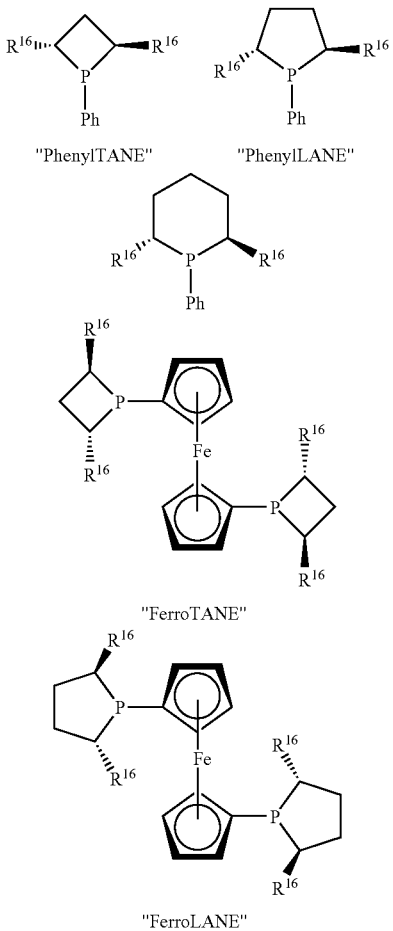

"PhenylTANE"  "PhenylLANE"

"FerroTANE"

"FerroLANE"

wherein $R^{16}$ is $C_{1-4}$ alkyl or aryl;
or the corresponding enantiomers thereof.

In a second embodiment of the process of the present invention, the chiral bisphosphine ligand has the following structural formula:

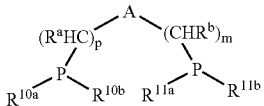

wherein m and p are each 0 or 1;
$R^a$ and $R^b$ are each independently hydrogen, $C_{1-4}$ alkyl, or $C_{3-6}$ cycloalkyl;
A represents (a) a $C_{1-5}$ alkylene bridge optionally containing one to two double bonds said $C_{1-5}$ alkylene bridge being unsubstituted or substituted with one to four substituents independently selected from the group consisting of $C_{1-4}$ alkyl, $C_{1-4}$ alkoxy, aryl, and $C_{3-6}$ cycloalkyl and said $C_{1-5}$ alkylene bridge being optionally fused with two $C_{5-6}$ cycloalkyl, $C_{6-10}$ aryl, or $C_{6-10}$ heteroaryl groups unsubstituted or substituted with one to four substituents independently selected from the group consisting of $C_{1-4}$ alkyl, $C_{1-4}$ alkoxy, chloro, and fluoro; (b) a 1,2-$C_{3-8}$ cycloalkylene bridge optionally containing one to three double bonds and one to two heteroatoms selected from $NC_{0-4}$ alkyl, $N(CH_2)_{0-1}Ph$, $NCOC_{1-4}$ alkyl, $NCOOC_{1-4}$ alkyl, oxygen, and sulfur and said 1,2-$C_{3-8}$ cycloalkylene bridge being unsubstituted or substituted with one to four substituents independently selected from the group consisting of $C_{1-4}$ alkyl, $C_{1-4}$ alkoxy, oxo, aryl, and $C_{3-6}$ cycloalkyl; (c) a 1,3-$C_{3-8}$ cycloalkylene bridge optionally containing one to three double bonds and one to two heteroatoms selected from $NC_{0-4}$ alkyl, $N(CH_2)_{0-1}Ph$, $NCOC_{1-4}$ alkyl, $NCOOC_{1-4}$ alkyl, oxygen, and sulfur and said 1,3-$C_{3-8}$ cycloalkylene bridge being unsubstituted or substituted with one to four substituents independently selected from the group consisting of $C_{1-4}$ alkyl, $C_{1-4}$ alkoxy, oxo, aryl, and $C_{3-6}$ cycloalkyl; or (d) 1,2-phenylene unsubstituted or substituted with one to three substituents independently selected from halogen, $C_{1-4}$ alkyl, hydroxy, and $C_{1-4}$ alkoxy; and $R^{10a}$, $R^{10b}$, $R^{11a}$, and $R^{11b}$ are each independently $C_{1-6}$ alkyl, $C_{3-6}$ cycloalkyl, or aryl with alkyl, cycloalkyl, and aryl being unsubstituted or substituted with one to three groups independently selected from the group consisting of $C_{1-4}$ alkyl, $C_{1-4}$ alkoxy, chloro, and fluoro; or $R^{10a}$ and $R^{10b}$ when taken together or $R^{11a}$ and $R^{11b}$ when taken together can form a 4- to 7-membered cyclic aliphatic ring unsubstituted or substituted with two to four substituents independently selected from the group consisting of $C_{1-4}$ alkyl, $C_{1-4}$ alkoxy, hydroxymethyl, $C_{1-4}$ alkoxymethyl, aryl, and $C_{3-6}$ cycloalkyl and said cyclic aliphatic ring being optionally fused with one or two aryl groups;
with the proviso that the chiral bisphosphine ligand is not a ligand selected from the group consisting of:
1,2-bis(anisylphenylphosphino)ethane (DIPAMP);
1,2-bis(alkylmethylphosphino)ethane (BisP*);
2,3-bis(diphenylphosphino)butane (CHIRAPHOS);
1,2-bis(diphenylphosphino)propane (PROPHOS);
2,3-bis(diphenylphosphino)-5-norbornene (NORPHOS);
2,3-O-isopropylidene-2,3-dihydroxy-1,4-bis-(diphenylphosphino)butane (DIOP);
1-cyclohexyl-1,2-bis(diphenylphosphino)ethane (CYCPHOS);
1-substituted-3,4-bis(diphenylphosphino)pyrrolidine (DEGPHOS);
2,4-bis(diphenylphosphino)pentane (SKEWPHOS);
1,2-bis(substituted phospholano)benzene (DuPHOS);
1,2-bis(substituted phospholano)ethane (BPE);
1-(substituted phospholano)-2-(diphenylphosphino)benzene (UCAP-Ph);
1-(bis(3,5-dimethylphenyl)phosphino)-2-(substituted phospholano)benzene (UCAP-DM);
1-(substituted phospholano)-2-(bis(3,5-di(t-butyl)-4-methoxyphenyl)phosphino)benzene (UCAP-DTBM); and
1-(substituted phospholano)-2-(di-naphthalen-1-yl-phosphino)benzene (UCAP-(1-Nap)).

In one class of this embodiment, $R^{10a}$ and $R^{10b}$ represent the same substituent which are both structurally distinct from $R^{11a}$ and $R^{11b}$ which represent the same but structurally distinct substituent. In a subclass of this class, $R^{10a}$ and $R^{10b}$ are both optionally substituted $C_{1-6}$ alkyl, and $R^{11a}$ and $R^{11b}$ are both optionally substituted $C_{3-6}$ cycloalkyl. In a second subclass of this class, $R^{10a}$ and $R^{10b}$ are both optionally substituted aryl, and $R^{11a}$ and $R^{11b}$ are both optionally substituted $C_{3-6}$ cycloalkyl. In a third subclass of this class, $R^{10a}$ and $R^{10b}$ are both substituted aryl, and $R^{11a}$ and $R^{11b}$ are both unsubstituted aryl. In a fourth subclass of this class, $R^{10a}$ and $R^{10b}$ are both optionally substituted $C_{1-6}$ alkyl, and $R^{11a}$ and $R^{11b}$ are both optionally substituted aryl.

A second class of this second embodiment encompasses chiral bisphosphine ligands disclosed in U.S. Pat. No. 4,994,615, the contents of which are incorporated by reference herein in their entirety. Non-limiting embodiments of this class of chiral 1,4-bisphosphine ligands are represented by structural formulae:

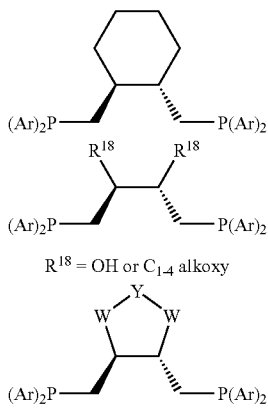

(i) W = O; Y = CH$_2$, CHMe, CMe$_2$, or CMeCH$_2$OH;
(ii) W = NC$_{1-4}$alkyl; Y = C(O);

or the corresponding enantiomers thereof.

Representative, but non-limiting, specific embodiments of this class of chiral bisphosphine ligands are the following structures:

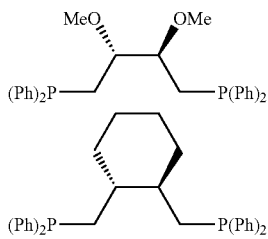

or the corresponding enantiomers thereof.

A third class of this second embodiment encompasses chiral bisphosphine ligands disclosed in U.S. Pat. Nos. 5,008,457; 5,171,892; 5,206,398; 5,329,015; 5,532,395; 5,386,061; 5,559,267; 5,596,114; and 6,492,544, the contents of all of which are incorporated by reference herein in their entirety. Non-limiting embodiments of this class of chiral bisphosphine ligands are represented by:

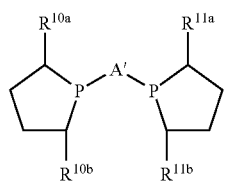

A′ = CH$_2$; CH$_2$CH$_2$; 1,2-phenylene; 2,5-furandione-3,4-diyl; or N—Me-2,5-pyrroledione-3,4-diyl;
R$^{10a}$, R$^{10b}$, R$^{11a}$, and R$^{11b}$ are each independently C$_{1-4}$ alkyl, C$_{1-4}$ alkoxy, CH$_2$OH, or CH$_2$OC$_{1-4}$ alkyl.

Representative, but non-limiting, specific embodiments of this class of chiral bisphosphine ligands are the following structures:

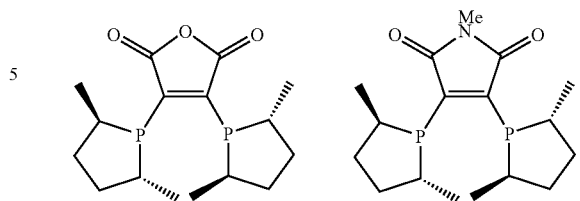

or the corresponding enantiomers thereof.

A fourth class of this second embodiment encompasses bisphosphine ligands of the structural formula:

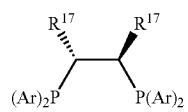

wherein Ar is aryl and R$^{17}$ is C$_{1-4}$ alkyl or aryl;
or the corresponding enantiomers thereof;
with the proviso that when Ar is unsubstituted phenyl, R$^{17}$ is not methyl.

A third embodiment of the chiral bisphosphine ligand encompasses biaryl or biheteroaryl bisphosphine ligands of the structural formulae:

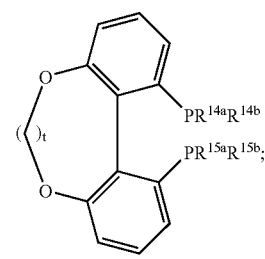

t = 1-6

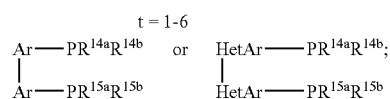

wherein Ar is phenyl or naphthyl unsubstituted or substituted with one to four substituents independently selected from C$_{1-4}$ alkyl, C$_{1-4}$ alkoxy, chloro, and fluoro; or two adjacent substituents on Ar together with the carbon atoms to which they are attached form a five-membered methylenedioxy ring;

HetAr is pyridyl or thienyl each of which is unsubstituted or substituted with one to four substituents independently selected from C$_{1-4}$ alkyl, C$_{1-4}$ alkoxy, chloro, and fluoro; or two adjacent substituents on HetAr together with the carbon atoms to which they are attached form a five-membered methylenedioxy ring;

R$^{14a}$, R$^{14b}$, R$^{15a}$, and R$^{15b}$ are each independently C$_{1-4}$ alkyl, aryl, or C$_{3-6}$ cycloalkyl wherein aryl and cycloalkyl are unsubstituted or substituted with one to four substituents independently selected from C$_{1-4}$ alkyl and C$_{1-4}$ alkoxy; or or R$^{14a}$ and R$^{14b}$ when taken together or R$^{15a}$ and R$^{15b}$ when taken together can form a 4- to 7-membered cyclic aliphatic ring unsubstituted or substituted with two to four substituents independently selected from the group consisting of C$_{1-4}$ alkyl, $C_{1-4}$ alkoxy, hydroxymethyl, $C_{1-4}$ alkoxymethyl, aryl, and $C_{3-6}$ cycloalkyl and said cyclic aliphatic ring being optionally fused with one or two aryl groups;

with the proviso that the chiral bisphosphine ligand is not a ligand selected from the group consisting of:

2,2'-bis(diphenylphosphino)-1,1'-binaphthyl (BINAP);

2,2'-bis(di-p-tolylphosphino)-1,1'-binaphthyl (TOL-BINAP);

2,2'-bis(di(3,5-dimethylphenyl)phosphino)-1,1'-binaphthyl (DM-BINAP);

2,2'-bis(diphenylphosphino)-6,6'-dimethyl-1,1'-biphenyl (BICHEP);

((5,6),(5',6')-bis(methylenedioxy)biphenyl-2,2'-diyl)(bis-diphenylphosphine) (SEGPHOS);

((5,6),(5',6')-bis(methylenedioxy)biphenyl-2,2'-diyl)(bis(3,5-dimethylphenyl)phosphine) (DM-SEGPHOS); and ((5,6),(5',6')-bis(methylenedioxy)biphenyl-2,2'-diyl)(bis(3,5-di(t-butyl)phenyl)phosphine) (DTBM-SEGPHOS).

In one class of this embodiment, $R^{14a}$ and $R^{14b}$ represent the same substituent which are both structurally distinct from $R^{15a}$ and $R^{15b}$ which represent the same but structurally distinct substituent. In a subclass of this class, $R^{14a}$ and $R^{14b}$ are both optionally substituted $C_{1-6}$ alkyl, and $R^{15a}$ and $R^{15b}$ are both optionally substituted $C_{3-6}$ cycloalkyl. In a second subclass of this class, $R^{14a}$ and $R^{14b}$ are both optionally substituted aryl, and $R^{15a}$ and $R^{15b}$ are both optionally substituted $C_{3-6}$ cycloalkyl. In a third subclass of this class, $R^{14a}$ and $R^{14b}$ are both substituted aryl, and $R^{15a}$ and $R^{15b}$ are both unsubstituted aryl. In a fourth subclass of this class, $R^{14a}$ and $R^{14b}$ are both optionally substituted $C_{1-6}$ alkyl, and $R^{15a}$ and $R^{15b}$ are both optionally substituted aryl.

Representative, but non-limiting, examples of this third embodiment of chiral bisphosphine ligands are the following structures:

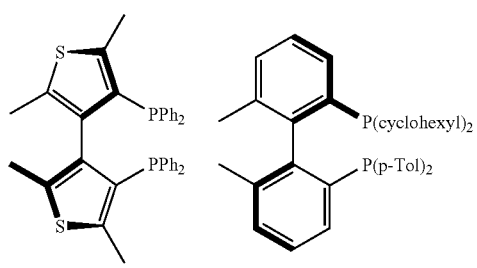

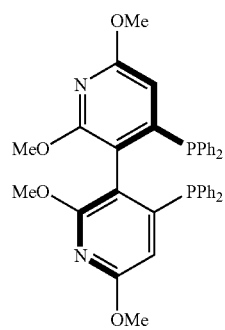

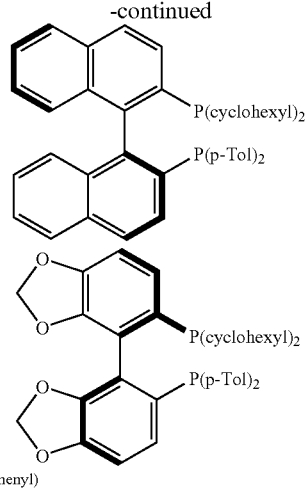

(p-Tol is p-methylphenyl)

or the corresponding enantiomers thereof.

A fourth embodiment encompasses chiral bisphosphine ligands disclosed in U.S. Pat. Nos. 5,874,629 and 6,043,387, the contents of both of which are incorporated by reference herein in their entirety. Non-limiting sub-embodiments of this embodiment of chiral bisphosphine ligands are represented by:

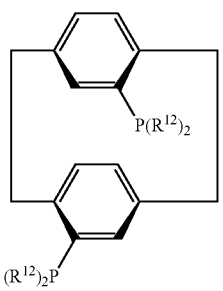

$R^{12} = C_{1-4}$ alkyl, $C_{3-6}$ cycloalkyl, or aryl or the corresponding enantiomers thereof.

A specific, but non-limiting, example of this embodiment of bisphosphine ligands is the following compound:

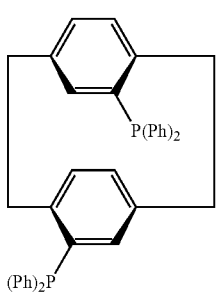

or the corresponding enantiomer thereof.

In a fifth embodiment of the process of the present invention, the chiral bisphosphine ligand has the following structural formula:

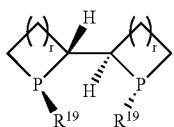

wherein r is 1, 2, or 3; and $R^{19}$ is $C_{1-4}$ alkyl or aryl;
or the corresponding enantiomers thereof.

A specific, but non-limiting, example of this embodiment of chiral bisphosphine ligands is the following:

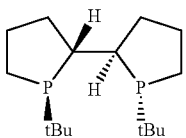

or the corresponding enantiomer thereof.

In a sixth embodiment of the process of the present invention, the chiral phosphine ligand is of the structural formula:

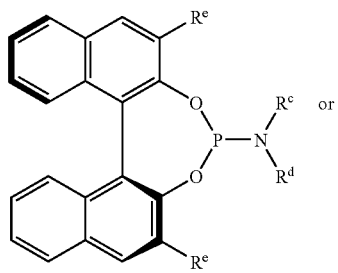

wherein $R^e$ is hydrogen or methyl; $R^c$ and $R^d$ are each independently hydrogen, $C_{1-4}$ alkyl, benzyl, or α-methylbenzyl; or $R^c$ and $R^d$ together with the nitrogen atom to which they are attached form a pyrrolidine or piperidine ring.

In a seventh embodiment of the process of the present invention, the chiral bisphosphine ligand is a ferrocenyl bisphosphine ligand of the structural formula:

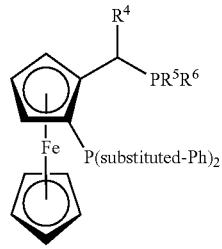

wherein $R^4$ is $C_{1-4}$ alkyl or aryl; and
$R^5$ and $R^6$ are each independently $C_{1-6}$ alkyl, $C_{5-12}$ cycloalkyl, or aryl.

In a class of this embodiment the carbon stereogenic center marked with an ** has the (R)-configuration as depicted in the structural formula:

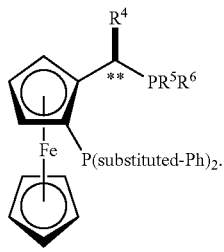

In a subclass of this class, $R^4$ is methyl or ethyl and $R^5$ and $R^6$ are $C_{1-4}$ alkyl. In a subclass of this subclass, $R^4$ is methyl and $R^5$ and $R^6$ are t-butyl.

The term "substituted-Ph" is intended to mean a phenyl group wherein at least one of the five carbon positions of the aromatic ring is substituted with a group independently selected from halogen, $C_{1-4}$ alkyl, $C_{1-4}$ alkoxy, $C_{1-4}$ alkylthio, and $C_{1-4}$ alkylsulfonyl wherein the alkyl group in each is unsubstituted or substituted with one to five fluorines. In one embodiment, "substituted-Ph" is 4-fluorophenyl or 4-(trifluoromethyl)phenyl.

Chiral ferrocenyl bisphosphine ligands encompassed within the process of the present invention are disclosed in U.S. Pat. Nos. 5,371,256; 5,463,097; 5,466,844; 5,563,308; 5,563,309; 5,565,594; 5,583,241; and RE37,344, the contents of all of which are incorporated by reference herein in their entirety.

In another aspect of the process of the present invention, $R^1$ is benzyl wherein the phenyl group of benzyl is unsubstituted or substituted one to five substituents selected from the group consisting of fluorine, trifluoromethyl, and trifluoromethoxy. In another embodiment of the process of the present invention, Z is $OR^2$ or $NR^2R^3$. In a class of this embodiment, $NR^2R^3$ is a heterocycle of the structural formula VI:

(VI)

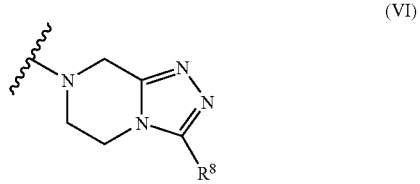

wherein $R^8$ is hydrogen or $C_{1-4}$ alkyl which is unsubstituted or substituted with one to five fluorines.

The asymmetric hydrogenation reaction of the present invention is carried out in a suitable organic solvent. Suitable organic solvents include lower alkanols, such as methanol, ethanol, and isopropyl alcohol; 2,2,2-trifluoroethanol (TFE); hexafluoroisopropyl alcohol; phenol; fluorinated phenols; polyhydroxylated benzenes, such as 1,2,3-trihydroxybenzene (pyrogallol) and 1,2,3,4-tetrahydroxybenzene; tetrahydrofuran; dichloromethane; methyl t-butyl ether; and mixtures thereof.

In one embodiment of the process of the present invention, the asymmetric hydrogenation reaction is also carried out in the presence of about 0.01 to about 10 mol % (relative to the prochiral enamine substrate of formula II) of an ammonium salt. In one embodiment the ammonium salt is an ammonium halide salt selected from the group consisting of ammonium chloride, ammonium bromide, and ammonium iodide. In a class of this embodiment the ammonium halide salt is ammonium chloride. In another embodiment the ammonium salt is an ammonium carboxylate salt such as ammonium acetate and ammonium formate. In another embodiment the ratio of the ammonium salt to prochiral enamine substrate is about 0.05 to about 5 mol %.

The reaction temperature for the reaction may be in the range of about 10° C. to about 90° C. A preferred temperature range for the reaction is about 45° C. to about 65° C.

The hydrogenation reaction can be performed at a hydrogen pressure range of about 0 psig to about 1500 psig. A preferred hydrogen pressure range is about 80 psig to about 200 psig.

The rhodium metal precursor is [Rh(monoolefin)2Cl]2, [Rh(diolefin)Cl]2, [Rh(monoolefin)2acetylacetonate], [Rh(diolefin)acetylacetonate], [Rh(monoolefin)4]X, or [Rh(diolefin)2]X wherein X is a non-coordinating anion selected from the group consisting of methanesulfonate, trifluoromethanesulfonate (Tf), tetrafluoroborate (BF4), hexafluorophosphate (PF6), or hexafluoroantimonate (SbF6). In one embodiment the rhodium metal precursor is [Rh(cod)Cl]$_2$, [Rh(norbornadiene)Cl]$_2$, [Rh(cod)$_2$]X, or [Rh(norbornadiene)$_2$]X. In a class of this embodiment, the rhodium metal precursor is [Rh(cod)Cl]$_2$.

The ratio of rhodium metal precursor to substrate is about 0.01 to about 10 mol %. A preferred ratio of the rhodium metal precursor to the substrate is about 0.05 mol % to about 0.4 mol %.

The beta amino acrylic acid derivative substrates of formula II for the asymmetric hydrogenation contain an olefinic double bond, and unless specified otherwise, are meant to include both E and Z geometric isomers or mixtures thereof as starting materials. The squiggly bond in the substrate of structural formula II signifies either the Z or E geometric isomer or a mixture thereof.

In one embodiment of the present invention, the geometric configuration of the double bond in the beta amino acrylic acid derivative substrate for the asymmetric hydrogenation reaction is the Z-configuration as depicted in formula VII:

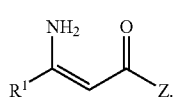

(VII)

Under the conditions for the preparation of the beta amino acrylic acid substrates for the asymmetric hydrogenation reaction, the Z-isomer is readily obtained via direct crystallization from the reaction mixture. The Z-configuration of the substrates is determined by nuclear magnetic resonance (NMR) methods, such as by nuclear Overhauser effect (NOE) experiments.

The beta amino acrylate esters of formula II (Z=OR$^2$ or SR$^2$) for the asymmetric hydrogenation reaction of the present invention can be prepared from a beta-keto ester of structural formula VI in high yield by reaction with a source of ammonia in a suitable organic solvent such as methanol, ethanol, isopropyl alcohol, tetrahydrofuran, and aqueous mixtures thereof.

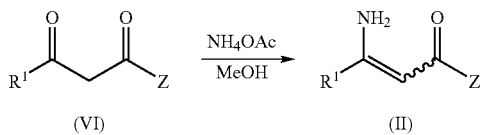

Sources of ammonia include ammonium acetate, ammonium hydroxide, and ammonium formate. In one embodiment the source of ammonia is ammonium acetate. The beta-keto esters can be prepared as described by D. W. Brooks et al., *Angew. Chem. Int. Ed. Engl.*, 18: 72 (1979).

The beta amino acrylamides can be prepared from the corresponding esters via amide exchange as described in *Org. Syn. Collect.*, Vol. 3, p. 108.

Throughout the instant application, the following terms have the indicated meanings:

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

The process of the present invention provides compounds of structural formula I with high optical purity, typically in excess of 50% ee. In one embodiment, compounds of formula I are obtained with an optical purity in excess of 70% ee. In a class of this embodiment, compounds of formula I are obtained with an optical purity in excess of 80% ee. In a subclass of this class, compounds of formula I are obtained with an optical purity in excess of 90% ee.

The term "enantioselective" shall mean a reaction in which one enantiomer is produced (or destroyed) more rapidly than the other, resulting in the predominance of the favored enantiomer in the mixture of products.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like. The alkyl groups are unsubstituted or substituted with one to three groups independently selected from the group consisting of halogen, hydroxy, carboxy, aminocarbonyl, amino, $C_{1-4}$ alkoxy, and $C_{1-4}$ alkylthio.

The term "cycloalkyl" is intended to mean cyclic rings of alkanes of five to twelve total carbon atoms, or any number within this range (i.e., cyclopentyl, cyclohexyl, cycloheptyl, etc).

The term "$C_{1-5}$ alkylene" is intended to mean a methylene ($-CH_2-$), ethylene ($-CH_2CH_2-$), propylene ($-CH_2CH_2CH_2-$), butylene ($-CH_2CH_2CH_2CH_2-$), or a pentylene ($-CH_2CH_2CH_2CH_2CH_2-$) group.

The term "1,2-phenylene" is intended to mean a phenyl group substituted at the 1- and 2-positions.

The term "1,2-$C_{3-8}$ cycloalkylene" is intended to mean a cycloalkyl group of 3- to 8-carbons which is substituted at adjacent carbons of the ring, as exemplified by 1,2-disubstituted cyclohexyl and 1,2-disubstituted cyclopentyl. The cycloalkylene group is also intended to encompass a bicyclic ring system containing one pair of bridgehead carbon atoms, such as a bicyclo[2.2.1]heptyl ring system (exemplified by norbornane and norbornene) and a bicyclo[2.2.2]octyl ring system.

The term "1,3-$C_{3-8}$ cycloalkylene" is intended to mean a cycloalkyl group of 3- to 8-carbons which is substituted at the 1- and 3-positions of the cylic ring system, as exemplified by 1,3-disubstituted cyclohexyl and 1,3-disubstituted cyclopentyl.

The term "halogen" is intended to include the halogen atoms fluorine, chlorine, bromine, and iodine.

The term "olefin" refers to a acyclic or cyclic hydrocarbon containing one or more double bonds including aromatic cyclic hydrocarbons. The term includes, but is not limited to, 1,5-cyclooctadiene ("cod") and norbornadiene ("nbd").

The abbreviation "cod" means "1,5-cyclooctadiene."

The term "aryl" includes phenyl or naphthyl. Unless specified, "aryl" is unsubstituted or substituted with one to five substituents independently selected from phenyl, halogen, hydroxy, amino, carboxy, $C_{1-4}$ alkyl, $C_{1-4}$ alkoxy, $C_{1-4}$ alkylthio, $C_{1-4}$ alkylsulfonyl, and $C_{1-4}$ alkyloxycarbonyl, wherein the alkyl moiety of each is unsubstituted or substituted with one to five fluorines.

The term "heteroaryl" means a 5- or 6-membered aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include, but are not limited to, pyrrolyl, isoxazolyl, isothiazolyl, pyrazolyl, pyridinyl, oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, and dibenzofuranyl. "Heteroaryl" is unsubstituted or substituted with one to five substituents independently selected from fluoro, hydroxy, trifluoromethyl, amino, $C_{1-4}$ alkyl, and $C_{1-4}$ alkoxy.

Representative experimental procedures utilizing the novel process are detailed below. The following Examples are for the purposes of illustration only and are not intended to limit the process of the present invention to the specific conditions for making these particular compounds.

EXAMPLE 1

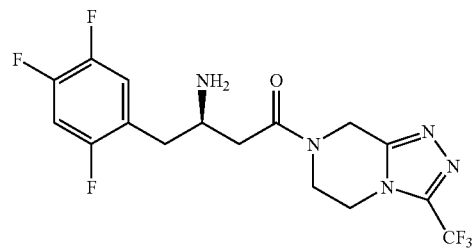

(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2-5)

Preparation of 3-(trifluoromethyl)-5,6,7,8-tetrahydro[1,2,4]triazolo[4,3-a]pyrazine, hydrochloride salt (1-4)

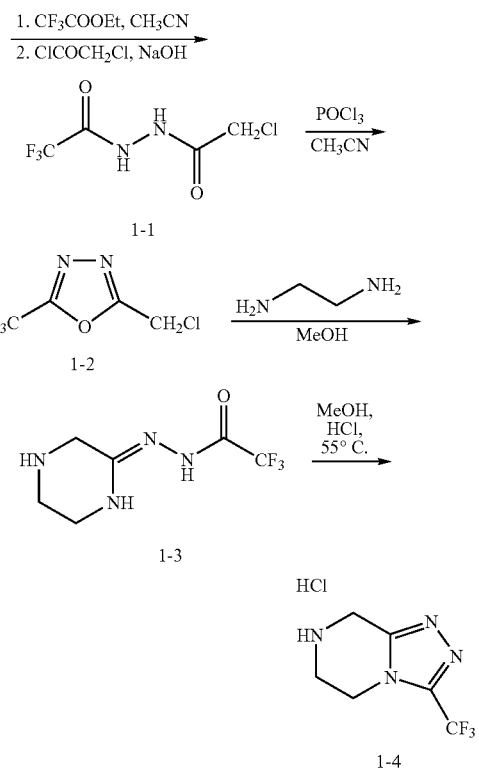

Step A: Preparation of bishydrazide (1-1)

Hydrazine (20.1 g, 35 wt % in water, 0.22 mol) was mixed with 310 mL of acetonitrile. 31.5 g of ethyl trifluoroacetate (0.22 mol) was added over 60 min. The internal temperature was increased to 25° C. from 14° C. The resulting solution was aged at 22-25° C. for 60 min. The solution was cooled to 7° C. 17.9 g of 50 wt % aqueous NaOH (0.22 mol) and 25.3 g of chloroacetyl chloride (0.22 mol) were added simultaneously over 130 min at a temperature below 16° C. When the reaction was complete, the mixture was vacuum distilled to remove water and ethanol at 27~30° C. and under 26~27 in Hg vacuum. During the distillation, 720 mL of acetonitrile was added slowly to maintain constant volume (approximately 500 mL). The slurry was filtered to remove sodium chloride. The cake was rinsed with about 100 mL of acetonitrile. Removal of the solvent afforded bis-hydrazide.

1H-NMR (400 MHz, DMSO-d6): δ 4.2 (s, 2H), 10.7 (s, 1H), and 11.6 (s, 1H) ppm. $^{13}$C-NMR (100 MHz, DMSO-$d_6$): δ 41.0, 116.1 (q, J=362 Hz), 155.8 (q, J=50 Hz), and 165.4 ppm.

Step B: Preparation of 5-(trifluoromethyl)-2-(chloromethyl)-1,3,4-oxadiazole (1-2)

Bishydrazide 1-1 from Step A (43.2 g, 0.21 mol) in ACN (82 mL) was cooled to 5° C. Phosphorus oxychloride (32.2 g, 0.21 mol) was added, maintaining the temperature below 10° C. The mixture was heated to 80° C. and aged at this temperature for 24 h until HPLC showed less than 2 area % of 1-1. In a separate vessel, 260 mL of IPAc and 250 mL of water were mixed and cooled to 0° C. The reaction slurry was charged to the quench keeping the internal temperature below 10° C. After the addition, the mixture was agitated vigorously for 30 min, the temperature was increased to room temperature and the aqueous layer was cut. The organic layer was then washed with 215 mL of water, 215 mL of 5 wt % aqueous sodium bicarbonate and finally 215 mL of 20 wt % aqueous brine solution. HPLC assay yield after work up was 86-92%. Volatiles were removed by distillation at 75-80 mm Hg, 55° C. to afford an oil which could be used directly in Step C without further purification. Otherwise the product can be purified by distillation to afford 1-2.

$^1$H-NMR (400 MHz, CDCl$_3$): δ 4.8 (s, 2H) ppm. $^{13}$C-NMR (100 MHz, CDCl$_3$): δ 32.1, 115.8 (q, J=337 Hz), 156.2 (q, J=50 Hz), and 164.4 ppm.

Step C: Preparation of N-[(2Z)-piperazin-2-ylidene]trifluoroacetohydrazide (1-3)

To a solution of ethylenediamine (33.1 g, 0.55 mol) in methanol (150 mL) cooled at −20° C. was added distilled oxadiazole 1-2 from Step B (29.8 g, 0.16 mol) while keeping the internal temperature at −20° C. After the addition was complete, the resulting slurry was aged at −20° C. for 1 h. Ethanol (225 mL) was then charged and the slurry slowly warmed to −5° C. After 60 min at −5° C., the slurry was filtered and washed with ethanol (60 mL) at −5° C. Amidine 1-3 was obtained as a white solid.

$^1$H-NMR (400 MHz, DMSO-$d_6$): δ 2.9 (t, 2H), 3.2 (t, 2H), 3.6 (s, 2H), and 8.3 (b, 1H) ppm. $^{13}$C-NMR (100 MHz, DMSO-$d_6$): δ 40.8, 42.0, 43.3, 119.3 (q, J=350 Hz), 154.2, and 156.2 (q, J=38 Hz) ppm.

Step D: Preparation of 3-(trifluoromethyl)-5,6,7,8-tetrahydro[1,2,4]triazolo[4,3-a]pyrazine, hydrochloride salt (1-4)

A suspension of amidine 1-3 (27.3 g, 0.13 mol) in 110 mL of methanol was warmed to 55° C. 37% Hydrochloric acid (11.2 mL, 0.14 mol) was added over 15 min at this temperature. During the addition, all solids dissolved resulting in a clear solution. The reaction was aged for 30 min. The solution was cooled down to 20° C. and aged at this temperature until a seed bed formed (10 min to 1 h). 300 mL of MTBE was charged at 20° C. over 1 h. The resulting slurry was cooled to 2° C., aged for 30 min and filtered. Solids were washed with 50 mL of ethanol:MTBE (1:3) and dried under vacuum at 45° C.

$^1$H-NMR (400 MHz, DMSO-$d_6$): δ 3.6 (t, 2H), 4.4 (t, 2H), 4.6 (s, 2H), and 10.6 (b, 2H) ppm; $^{13}$C-NMR (100 MHz, DMSO-$d_6$): δ 39.4, 39.6, 41.0, 118.6 (q, J=325 Hz), 142.9 (q, J=50 Hz), and 148.8 ppm.

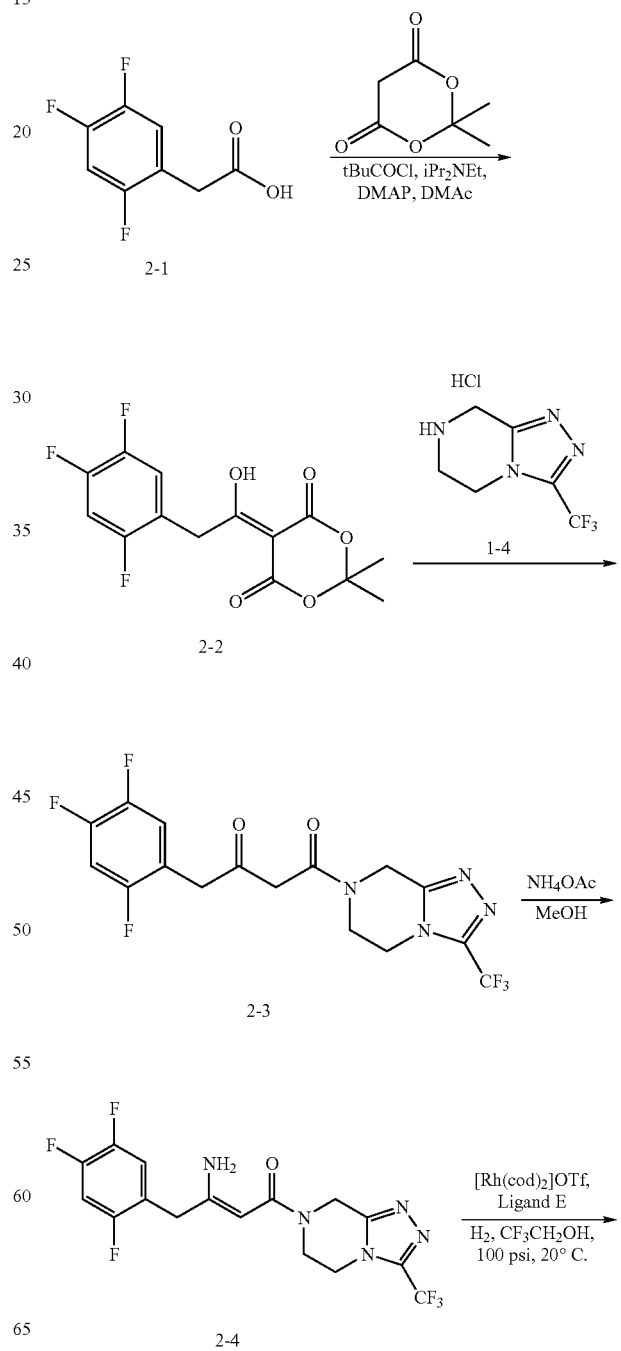

Scheme 2

-continued

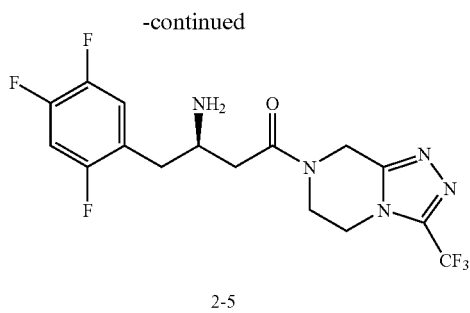

2-5

Step A: Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (2-3)

2,4,5-Trifluorophenylacetic acid (2-1) (150 g, 0.789 mol), Meldrum's acid (125 g, 0.868 mol), and 4-(dimethylamino)pyridine (DMAP) (7.7 g, 0063 mol) were charged into a 5 L three-neck flask. N,N-Dimethylacetamide (DMAc) (525 mL) was added in one portion at room temperature to dissolve the solids. N,N-diisopropylethylamine (282 mL, 1.62 mol) was added in one portion at room temperature while maintaining the temperature below 40° C. Pivaloyl chloride (107 mL, 0.868 mol) was added dropwise over 1 to 2 h while maintaining the temperature between 0 and 5° C. The reaction mixture was aged at 5° C. for 1 h. Triazole hydrochloride 1-4 (180 g, 0.789 mol) was added in one portion at 40-50° C. The reaction solution was aged at 70° C. for several h. 5% Aqueous sodium hydrogencarbonate solution (625 mL) was then added dropwise at 20-45° C. The batch was seeded and aged at 20-30° C. for 1-2 h. Then an additional 525 mL of 5% aqueous sodium hydrogencarbonate solution was added dropwise over 2-3 h. After aging several h at room temperature, the slurry was cooled to 0-5° C. and aged 1 h before filtering the solid. The wet cake was displacement-washed with 20% aqueous DMAc (300 mL), followed by an additional two batches of 20% aqueous DMAc (400 mL), and finally water (400 mL). The cake was suction-dried at room temperature.

Step B: Preparation of (2Z)-4-oxo-4-[3-(trifluoromethyl)-5,6-dihydro[1,2,4]triazolo[4,3-a]pyrazin-7(8H)-yl]-1-(2,4,5-trifluorophenyl)but-2-en-2-amine (2-4)

A 5 L round-bottom flask was charged with methanol (100 mL), the ketoamide 2-3 (200 g), and ammonium acetate (110.4 g). Methanol (180 mL) and 28% aqueous ammonium hydroxide (58.6 mL) were then added keeping the temperature below 30° C. during the addition. Additional methanol (100 mL) was added to the reaction mixture. The mixture was heated at reflux temperature and aged for 2 h. The reaction was cooled to room temperature and then to about 5° C. in an ice-bath. After 30 min, the solid was filtered and dried to afford 2-4 as a solid; m.p. 271.2° C.

Step C: Preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2-5)

Into a flask was charged [Rh(cod)$_2$]OTf (0.1 mmol) and (S)-Cy2-p-Tol-Biphemp (Ligand E) (0.1 mmol) under a nitrogen atmosphere. Degassed trifluoroethanol was then added (20 mL) and the mixture was stirred at room temperature for 1 h. Into a hydrogenator was charged the enamine amide 2-4 (1 mmol) and then degassed. The catalyst solution was then transferred to the hydrogenator under nitrogen. After degassing three times, the enamine amide was hydrogenated under 100 psig hydrogen gas at 20° C. for 20 h (94% assay yield, 98% ee).

$^1$H NMR (300 MHz, CD$_3$CN): δ 7.26 (m), 7.08 (m), 4.90 (s), 4.89 (s), 4.14 (m), 3.95 (m), 3.40 (m), 2.68 (m), 2.49 (m), 1.40 (bs).

Compound 2-5 exists as amide bond rotamers. Unless indicated, the major and minor rotamers are grouped together since the carbon-13 signals are not well resolved:

$^{13}$C NMR (CD$_3$CN): δ 171.8, 157.4 (ddd, $J_{CF}$=242.4, 9.2, 2.5 Hz), 152.2 (major), 151.8 (minor), 149.3 (ddd; $J_{CF}$=246.7, 14.2, 12.9 Hz), 147.4 (ddd, $J_{CF}$=241.2, 12.3, 3.7 Hz), 144.2 (q, $J_{CF}$=38.8 Hz), 124.6 (ddd, $J_{CF}$=18.5, 5.9, 4.0 Hz), 120.4 (dd, $J_{CF}$=19.1, 6.2 Hz), 119.8 (q, $J_{CF}$=268.9 Hz), 106.2 (dd, $J_{CF}$=29.5, 20.9 Hz), 50.1, 44.8, 44.3 (minor), 43.2 (minor), 42.4, 41.6 (minor), 41.4, 39.6, 38.5 (minor), 36.9.

The following high-performance liquid chromatographic (HPLC) conditions were used to determine percent conversion to product:

Column: Waters Symmetry C18, 250 mm×4.6 mm
Eluent: Solvent A: 0.1 vol % HClO$_4$/H$_2$O
  Solvent B: acetonitrile
Gradient: 0 min 75% A: 25% B
  10 min 25% A: 75% B
  12.5 min 25% A: 75% B
  15 min 75% A: 25% B
Flow rate: 1 mL/min
Injection Vol.: 10 μL
UV detection: 210 nm
Column temp.: 40° C.
Retention times: compound 2-4: 9.1 min
  compound 2-5: 5.4 min The following high-performance liquid chromatographic (HPLC) conditions were used to determine optical purity:
Column: Chirapak, AD-H, 250 mm×4.6 mm
Eluent: Solvent A: 0.2 vol. % diethylamine in heptane
  Solvent B: 0.1 vol % diethylamine in ethanol
Isochratic Run Time: 18 min
Flow rate: 0.7 mL/min
Injection Vol.: 7 μL
UV detection: 268 nm
Column temp.: 35° C.
Retention times: (R)-amine 2-5: 13.8 min
  (S)-amine: 11.2 min

EXAMPLE 2

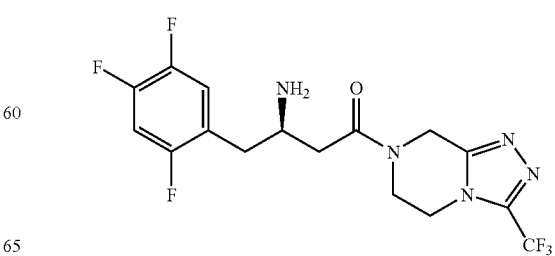

(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2-5)

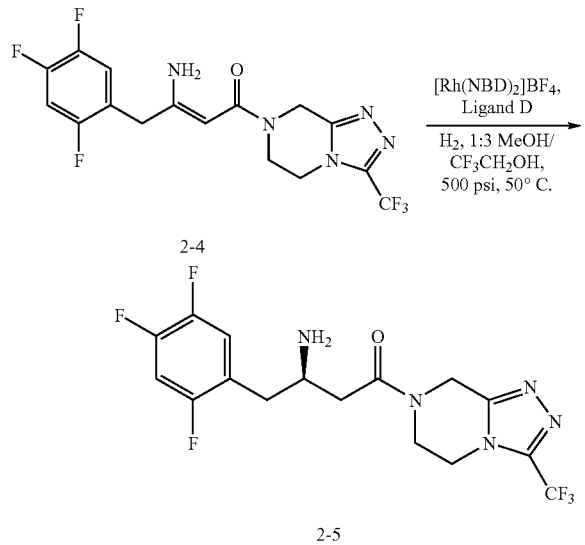

Into a flask were charged bis(norbornadiene)rhodium(I) tetrafluoroborate {[Rh(nbd)$_2$]BF$_4$}(41.55 mg, 0.1 mmol), Ligand D (69.73 mg, 0.1 mmol) and the enamine amide 2-4 (45 g, 111.1 mmol) under a nitrogen atmosphere. To this mixture a solvent mixture of 37.5 mL methanol (extra dry and degassed) and 112.5 mL 2,2,2-trifluoroethanol (distilled and degassed) were added. The slurry was then transferred under nitrogen into an stainless steel autoclave and sealed. The autoclave was then heated to 50° C. and pressurized to 500 psig with hydrogen. A sample taken after 17 hours was analyzed using HPLC, which confirmed the end of the reaction giving 94% assay yield and 94% ee.

EXAMPLES 3-5

TABLE 1[a]

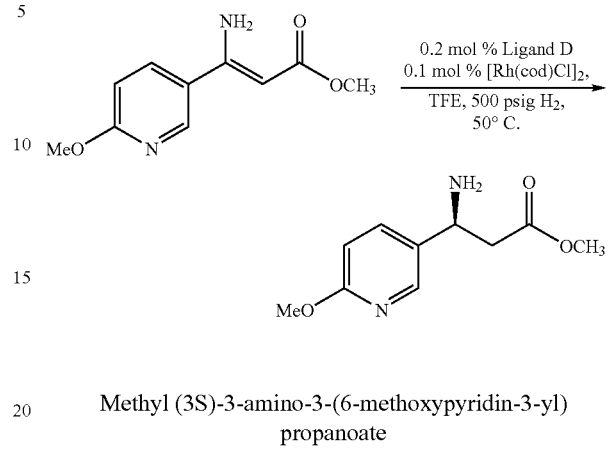

| Ex. | Ligand | Metal precursor | % yield[b] | % ee[c] | config. |
|---|---|---|---|---|---|
| 3 | A | [Rh(cod)$_2$]BF$_4$ | 77 | 88 | R |
| 4 | B | [Rh(cod)Cl]$_2$ | 58 | 76 | R |
| 5 | C | [Rh(cod)Cl]$_2$ | 15 | 78 | S |

[a]Reaction conditions: in TFE, 5 mol % metal precursor, 5 mol % ligand, 90 psig H$_2$, 50° C., 18 h;
[b]Assayed by HPLC;
[c]Assayed by chiral HPLC using a AS-RH chiral column eluting with 20% acetonitrile/water as the mobile phase.

EXAMPLE 6

Methyl (3S)-3-amino-3-(6-methoxypyridin-3-yl)propanoate

Into a 25 ml flask were charged chloro(1,5-cyclooctadiene)rhodium(I) dimer {[Rh(cod)Cl]2}(5.9 mg, 0.012 mmol) and (R,S)-p-CF3 Josiphos (Ligand D) (16.3 mg, 0.024 mmol) under a nitrogen atmosphere. Degassed and distilled 2,2,2-trifluoroethanol was then added (5 mL) and the mixture was stirred at room temperature for 40 min. Into a 25 mL hydrogenation vial was charged the enamine ester (3 g, 0.01441 mol) along with 2,2,2-trifluoroethanol (7 mL). After the enamine ester was dissolved, 3 mL of the catalyst solution was added to the hydrogenation vial (0.1 mol % catalyst). The hydrogenation vial was then sealed and transferred into the hydrogenation bomb under nitrogen. After degassing three times with hydrogen, the enamine ester was hydrogenated under 500-psig-hydrogen gas at 50° C. for 24 h.

Assay yield was determined by HPLC to be 96% and optical purity to be 97% ee (HPLC conditions same as for Example 1).

$^1$H-NMR (400 MHz, CDCl$_3$): δ 1.81 (bs, 2H), 2.64 (m, 2H), 3.68 (s, 3H), 3.91 (s, 3H), 4.4 (dd, 1H), 6.72 (d, 1H), 7.62 (dd, 1H), and 8.11 (s, 1H) ppm.

EXAMPLES 7-12

TABLE 2[a]

| Ex. | Ligand (L*) | R$^1$ | % yield[b] | % ee[c] | config. |
|---|---|---|---|---|---|
| 7 | D | Ph | 92 | 96 | S |
| 8 | D | 4-F-Ph | 62 | 96 | S |
| 9 | D | 4-OMe-Ph | 88 | 95 | S |
| 10 | D | 3-Pyridyl | 91 | 96 | S |
| 11 | D | PhCH$_2$— | 94 | 93 | S |
| 12 | D | 4-CF$_3$-Ph- | 94 | 97 | S |

[a]Reaction conditions: 0.15 mol % [Rh(cod)Cl]$_2$; 0.33 mol % ligand, 50° C., 100 psig H$_2$.
[b]Assay yield;
[c]Assayed by chiral HPLC using a AS-RH or AD-RH chiral column eluting with 25-40% acetonitrile/water as the mobile phase.

The structures of the chiral phosphine ligands employed in the Examples above are provided below:

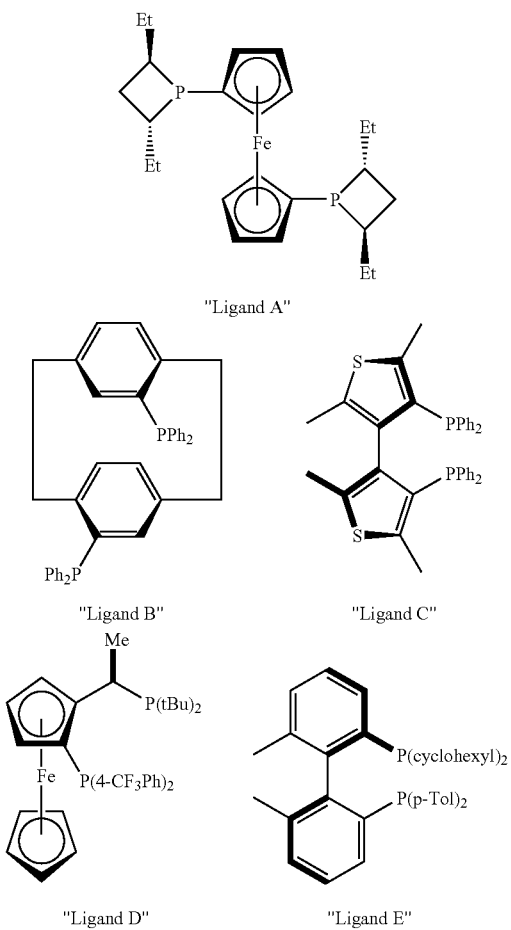

"Ligand A"

"Ligand B"    "Ligand C"

"Ligand D"    "Ligand E"

What is claimed is:

1. A process for preparing a compound of structural formula I:

(I)

enantiomerically enriched at the carbon atom marked with an *; wherein $Z$ is $OR^2$, $SR^2$, or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, N, NH, and $NC_{1-4}$ alkyl, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one to five fluorines; and said heterocyclic ring system being optionally fused with a 5- to 6-membered saturated or aromatic carbocyclic ring system or a 5- to 6-membered saturated or aromatic heterocyclic ring system containing one to three heteroatoms selected from O, S, N, NH, and $NC_{1-4}$ alkyl, said fused ring system being unsubstituted or substituted with one to four substituents selected from hydroxy, amino, fluorine, $C_{1-4}$ alkyl, and $C_{1-4}$ alkoxy, wherein alkyl and alkoxy are unsubstituted or substituted with one to five fluorines;

comprising the step of hydrogenating in the presence of hydrogen gas a prochiral enamine of structural formula II:

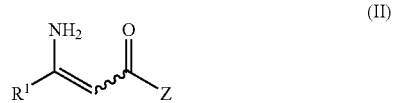
(II)

in a suitable organic solvent in the presence of a rhodium metal precursor complexed to a chiral phosphine ligand selected from the group consisting of:

(a) a ligand of the structural formula:

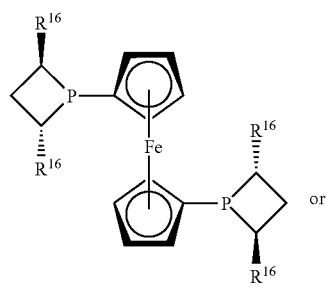
or
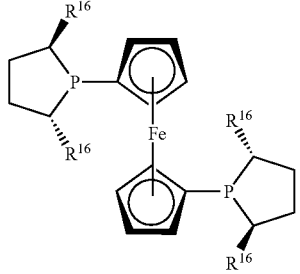

wherein $R^{16}$ is $C_{1-4}$ alkyl or aryl; or an enantiomer thereof;

(b) a ligand of the structural formula:

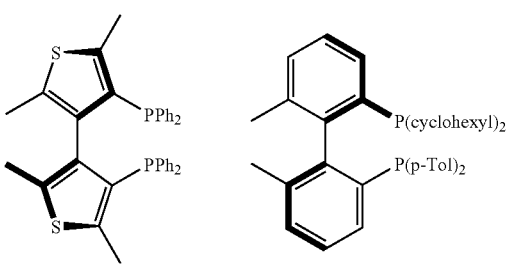

-continued

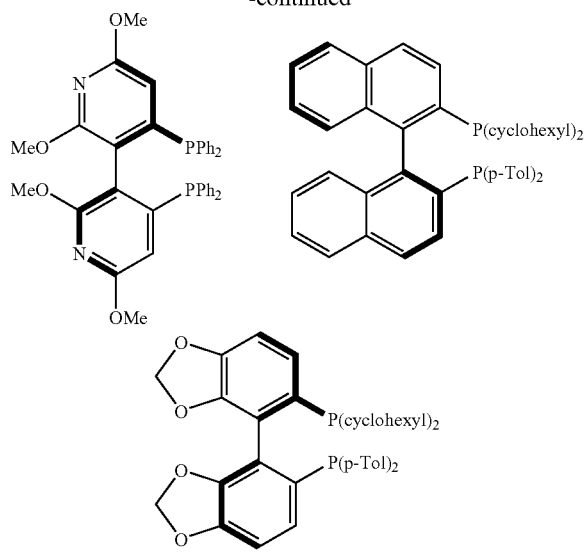

or an enantiomer thereof;

(c) a ligand of the structural formula:

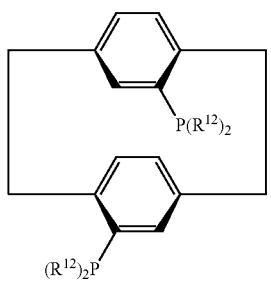

wherein $R^{12}$ is $C_{1-4}$ alkyl, $C_{3-6}$ cycloalkyl, or aryl; or an enantiomer thereof; and (d) a ligand of the structural formula:

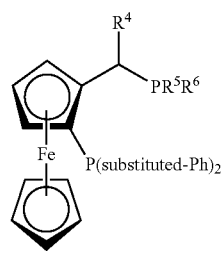

wherein $R^4$ is $C_{1-4}$ alkyl or aryl; and $R^5$ and $R^6$ are each independently $C_{1-6}$ alkyl, $C_{5-12}$ cycloalkyl, or aryl; and wherein said rhodium metal precursor is [Rh(monoolefin)$_2$Cl]$_2$, [Rh(diolefin)Cl]$_2$, [Rh(monoolefin)$_2$acetylacetonate], [Rh(diolefin)acetylacetonate], [Rh(monoolefin)$_4$]X, or [Rh(diolefin)$_2$]X wherein X is selected from the group consisting of methanesulfonate, trifluoromethanesulfonate, tetrafluoroborate, hexafluorophosphate, and hexafluoroantimonate.

2. The process of claim 1 wherein said chiral phosphine ligand is of the structural formula:

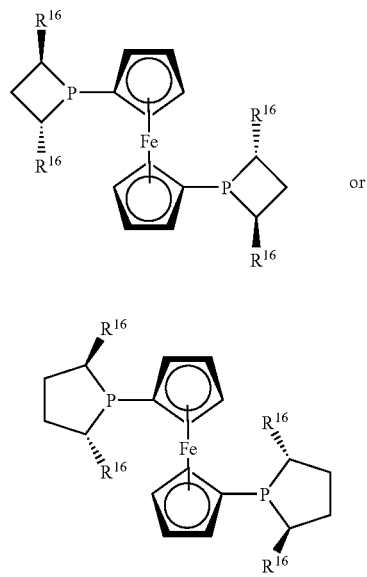

wherein $R^{16}$ is $C_{1-4}$ alkyl or aryl; or an enantiomer thereof.

3. The process of claim 1 wherein said chiral phosphine ligand is of the structural formula:

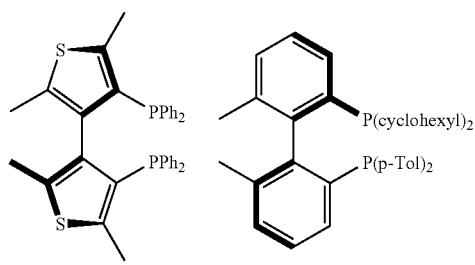

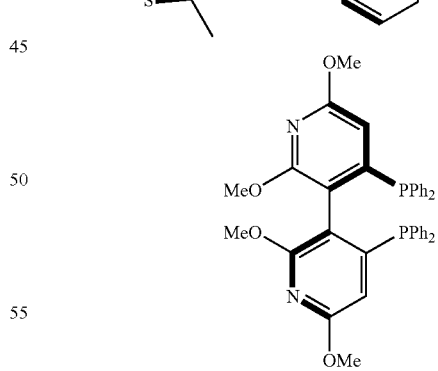

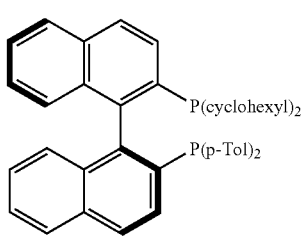

-continued

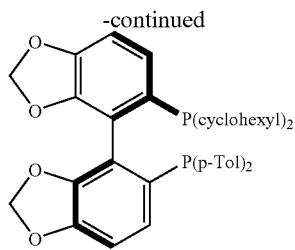

or an enantiomer thereof.

4. The process of claim 1 wherein said chiral phosphine ligand is of the structural formula:

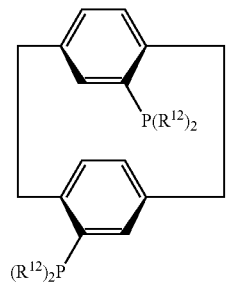

wherein $R^{12}$ is $C_{1-4}$ alkyl, $C_{3-6}$ cycloalkyl, or aryl; or an enantiomers thereof.

5. The process of claim 4 wherein aryl is phenyl.

6. The process of claim 1 wherein said chiral phosphine ligand is a ferrocenyl bisphosphine ligand of the structural formula:

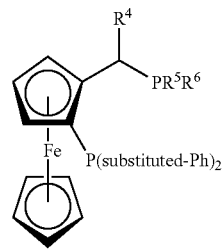

wherein $R^4$ is $C_{1-4}$ alkyl or aryl; and
$R^5$ and $R^6$ are each independently $C_{1-6}$ alkyl, $C_{5-12}$ cycloalkyl, or aryl.

7. The process of claim 6 wherein the carbon stereogenic center marked with an ** has the (R)-configuration as depicted in the structural formula:

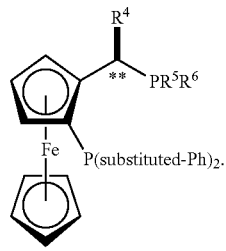

8. The process of claim 7 wherein $R^4$ is methyl or ethyl and $R^5$ and $R^6$ are $C_{1-4}$ alkyl.

9. The process of claim 8 wherein $R^4$ is methyl; $R^5$ and $R^6$ are t-butyl; and substituted-Ph is 4-fluorophenyl or 4-(trifluoromethyl)phenyl.

10. The process of claim 9 wherein $R^1$ is 6-methoxy-pyridin-3-yl and Z is $C_{1-4}$ alkoxy.

11. The process of claim 10 said rhodium metal precursor is $[Rh(cod)Cl]_2$.

12. The process of claim 1 wherein said hydrogenating step is carried in the presence of an ammonium salt.

13. The process of claim 12 wherein said ammonium salt is ammonium chloride.

14. The process of claim 1 wherein $R^1$ is benzyl wherein the phenyl group of benzyl is unsubstituted or substituted one to five substituents selected from the group consisting of fluorine, trifluoromethyl, and trifluoromethoxy.

15. The process of claim 1 wherein $NR^2R^3$ is a heterocycle of the structural formula VI:

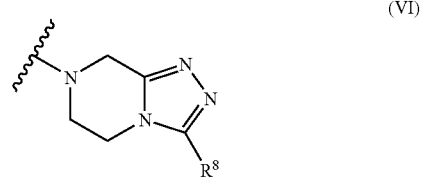

(VI)

wherein $R^8$ is hydrogen or $C_{1-4}$ alkyl which is unsubstituted or substituted with one to five fluorines.

* * * * *